(12) United States Patent
Nachman et al.

(10) Patent No.: US 6,207,643 B1
(45) Date of Patent: Mar. 27, 2001

(54) MIMETIC INSECT ALLATOSTATIN ANALOGS FOR INSECT CONTROL

(75) Inventors: Ronald J. Nachman, Willis, TX (US); Peter E. A. Teal, Gainesville, FL (US); Christopher S. Garside, Toronto; Stephen S. Tobe, Virgil, both of (CA)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/191,906

(22) Filed: Nov. 13, 1998

(51) Int. Cl.[7] .......................... A61K 38/08; A61K 38/10
(52) U.S. Cl. .......................... 514/14; 514/16; 514/17; 530/326; 530/327; 530/329; 530/330
(58) Field of Search .................... 530/226, 327, 530/329, 330; 514/14–17

(56) References Cited

U.S. PATENT DOCUMENTS

| | | | |
|---|---|---|---|
| 5,792,466 | 8/1998 | Nachman et al. | 424/405 |
| 5,795,857 | 8/1998 | Nachman et al. | 514/2 |

OTHER PUBLICATIONS

R.J. Nachman et al., "Active conformation and peptidase resistance of conformationally restricted analogues of the insect allatostatin neuropeptide family", presented at XIII International Congress of Comparative Endocrinology at Yokohama, Japan 16–21 of Nov. 1997.

C.S. Garside et al. "Catabolism of insect neuropeptides: allatostatin as models for peptidomimetic design", presented at XIII International Congress of Comparative Endocrinology at Yokohama, Japan 16–21 of Nov. 1997.

T.K. Hayes et al. "Structure–Activity Studies of Allatostatin 4 on the Inhibition of juvenile Hormone Biosynthesis by Corpora Allata: The Importance of Individual Side Chains and Stereochemistry", *Peptides*, vol. 15, No. 7, pp. 1165–1171, 1994.

R.J. Nachman et al. "Synthesis, Biological Activity, and Conformational Studies of Insect Allatostatin Neuropeptide Analogues Incorporating Turn–Promoting Moieties", *Bioorganic & Medical Chemistry 6* , pp. 1379–1388, 1988.

*Primary Examiner*—M. Borin
(74) *Attorney, Agent, or Firm*—M. Howard Silverstein; John D. Fado; Randall E. Deck (57) ABSTRACT

Novel pseudopeptide analogs of the insect allatostatin neuropeptide family which possess biological activity mimicking that of the naturally occurring neuropeptides are disclosed. By addition of a hydrophobic moiety to an active portion of the allatostatin peptides, analogs are produced which exhibit an overall amphiphilic nature and which are capable of penetrating the insect cuticle while still retaining biological activity. Furthermore, by substituting sterically hindered amino acids or aromatic acids for any or all of the first, third or fifth amino acid residues of the allatostatin C-terminal pentapeptide, analogs may be produced which are resistant to degradation by insect peptidases while still retaining biological activity. The analogs may be used for insect control by disrupting critical reproductive and/or developmental processes normally regulated by allatostatins in insects.

17 Claims, 4 Drawing Sheets

FIG 4

MIMETIC INSECT ALLATOSTATIN ANALOGS FOR INSECT CONTROL

BACKGROUND OF THE INVENTION

1. Field of Invention

This invention relates to mimetic pseudopeptide analogs of the allatostatin neuropeptide family, and the use of these analogs for insect control.

2. Description of the Prior Art

The allatostatin family of insect neuropeptides inhibit the in vitro biosynthesis of juvenile hormone (JH) by the corpora allata of the cockroaches *Diploptera punctata Blattella germanica* (L) and *Periplaneta americana* (Belles et al., 1994, Reg. Peptides, 53:237–247; and Weaver et al., 1994, Comp. Biochem. Physiol., 107(c):107–127). In these pests, JH plays a significant role in development reproductive maturity, sex pheromone production and mating. Specifically, a reduction in endogenous levels of JH is critical to development of the adult stage from the nymph in the cockroach, whereas oocyte growth and maturation in adult females show a dependency on the presence of JH (Bendena et al., Allatostatins: Diversity in structure and function of an insect neuropeptide family. In: Beckwith et al., Eds., Neuropeptides in Development and Aging, pp. 53–66, Annals NY Acad. Sci. 814: 53–66: 1997).

Although the allatostatins can influence a number of physiological processes by virtue of their ability to modulate in vitro production of JH, the native allatostatins have held little promise as insect control agents. The major limitations of the allatostatins which have hampered their use for insect control include their inability to penetrate the insect cuticle, and their susceptibility to inactivation by peptidases in the hemolymph and gut and/or bound to tissues within the insect (Bendena et al., ibid).

Earlier structure-activity studies have shown that the C-terminal pentapeptide $Xaa_3$-$Xaa_2$-Phe-Gly-$Xaa_2$-$NH_2$ (wherein $Xaa_1$ occurs as any of Asn, Asp, Gly, Ser or Ala, $Xaa_2$ occurs as Leu or Ile, and $Xaa_3$ occurs as Tyr or Phe) is shared by all members of the Diploptera allatostatins, and represents the 'active core' region or minimum sequence capable of eliciting inhibition of JH production in vitro (Hayes et al., Peptides, 15:1165–1171, 1994; Pratt et al., Biochem. Biophys. Res. Commun., 163:1243–247, 1989; and Pratt et al., Proc. Natl. Acad. Sci. USA, 88:2412–2416, 1991). The side chains of active core residues Phe, Leu and Tyr proved to be the most important for activity (Hayes et al., ibid). Recent studies have elucidated the primary catabolic cleavage sites of the allatostatins following incubation with hemolymph enzymes and with membrane peptidases in crude membrane preparations. Hemolymph enzymes primarily cleave the peptides in the N-terminal region outside of the pentapeptide core region and therefore, do not inactivate the allatostatins (Garside et al., Peptides, 18:17–25, 1997). However, membrane preparations of brain, gut and corpora allata cleave allatostatins at the C-terminus between residues Gly-Leu, with secondary cleavage occurring between the residue block $Xaa_3$-$Xaa_1$ (Garside et al., Gen. Comp. Endocrinol., 108:258–270, 1997). Both of these cleavages disrupt the active core sequence and lead to completely inactive fragments.

The contents of each of the above-mentioned publications are incorporated by reference herein.

SUMMARY OF THE INVENTION

We have discovered novel pseudopeptide analogs of the insect allatostatin neuropeptide family which possess biological activity mimicking that of the naturally occurring neuropeptides. By addition of a hydrophobic moiety to an active portion of the allatostatin peptides, analogs are produced which exhibit an overall amphiphilic nature and which are capable of penetrating the insect cuticle while still retaining biological activity. Furthermore, by substituting sterically hindered amino acids or aromatic acids for any or all of the second, third or fifth amino acid residues of the allatostatin C-terminal pentapeptide, analogs have been produced which are resistant to degradation by insect peptidases while still retaining biological activity. The analogs may be used for insect control by disrupting critical reproductive and/or developmental processes normally regulated by allatostatins in insects.

In accordance with this discovery, it is an object of this invention to provide novel compounds having biological activity mimicking that of the naturally occurring allatostatin neuropeptides.

It is also an object of this invention to provide compounds which are bioactive mimics of allatostatin neuropeptides that are capable of penetrating the insect cuticle.

Another object is to provide compounds which are bioactive mimics of allatostatin neuropeptides which are resistant to enzyme degradation.

Yet another object is to provide compounds which are bioactive mimics of allatostatin neuropeptides and their use for controlling insect populations and which may be topically applied.

Other objects and advantages of the invention will become readily apparent from the ensuing description.

BRIEF DESCRIPTION OF THE DRAWINGS

FIGS. 3(a) and (b) show the structures of peptidase resistant allatostatin analogs containing sterically hindered, restricted conformation components: a) both an indane ring (Aic) and cyclopropyl ring (Cpa), and b) benzodiazepine (Bzd).

DETAILED DESCRIPTION OF THE INVENTION

In the following description, the nomenclature used to define the peptides and pseudopeptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

Allatostatin analogs capable of penetrating the insect cuticle are prepared by conjugating a hydrophobic moiety to a member of the allatostatin insect neuropeptide family, or a bioactive portion thereof, to render the compound amphiphilic. These compounds are of the general formula I:

$$R\text{-}X_1\text{-}Phe\text{-}Gly\text{-}X_2\text{-}NH_2 \quad\quad (I)$$

wherein $X_1$ is Asn, Asp, Gly, Ser, or Ala, and $X_2$ is either Leu or Ile. The R moiety incorporates the hydrophobic functionality which is effective to impart the amphiphilic nature to the molecule.

In a first preferred embodiment, the compound is a pseudopentapeptide analog of the C-terminal allatostatin core region. In this embodiment, a hydrophobic carborane moiety is incorporated onto the N-terminus of the C-terminal pentapeptide, $Xaa_3\text{-}X_1\text{-}Phe\text{-}Gly\text{-}X_2\text{-}NH_2$ ($Xaa_3$ being Phe or Tyr), or the C-terminal tetrapeptide, $X_1\text{-}Phe\text{-}Gly\text{-}X_2\text{-}NH_2$. Specifically, o-, m- or p- carborane conjugated to a short chain alkanoyl-acyl group is conjugated to the N-terminal Tyr or Phe amino acid of the pentapeptide, or the N-terminal $X_1$ of the tetrapeptide. In a variation of this embodiment, the aromatic ring of the Tyr or Phe amino acid ($Xaa_3$) may be replaced by a carborane moiety, thereby forming carboranyl alanine of the formula:

$$\quad\quad (II)$$

Referring to formula I, in this first preferred embodiment R may therefore be shown as:

$$Cb\text{---}(CH_2)_n\text{---}C(O)\text{---}X_3' \quad\quad (III)$$

where Cb is a carborane, n is 1, 2 or 3, and $X_3'$ is Tyr, Phe, carboranyl alanine or a bond. When $X_3'$ is a bond, n is preferably 2.

In a second preferred embodiment, the allatostatins or an active C-terminal portion thereof containing at least the C-terminal pentapeptide $Xaa_3\text{-}X_1\text{-}Phe\text{-}Gly\text{-}X_2\text{-}NH_2$ ($Xaa_3$ being Phe or Tyr), are modified at their N-terminus by addition of a hydrophobic moiety which may be an aromatic amine, aromatic acid, or aliphatic fatty acid. A variety of hydrophobic aromatic amines and acids are suitable for use herein. Preferred acids include phenyl alkanoic, alkenoic or alkynoic acids such as 9-fluoreneacetic acid, 6-phenyl hexanoic acid or 9-phenyl nonanoic acid, while preferred amines include phenyl alkanoic, alkenoic or alkynoic amines such as 4-phenyl butyl amine. Without being limited thereto, examples of other suitable aromatic acids include 2-biphenylenecarboxylic acid, 9-anthracenecarboxylic acid, 1-fluorenecarboxylic acid, and 1-pyrenebutyric acid, while other suitable aromatic amines include 1-aminoanthracene, 6-amino-3,4-benzocoumarin, 2-amino-7-bromofluorene, 6-aminochrysene, 3-aminofluoranthene, 9-aminophenanthrene, and 1-pyrenemethylamine, and suitable aliphatic fatty acids include palmitic acid, caprylic acid, decanoic acid, lauric acid, and valeric acid. Optionally, the hydrophobic aromatic amines or acids or the aliphatic fatty acids may further include the amino acid Arg conjugated thereto.

The analog of this second embodiment may be prepared from any member of the allatostatin family of neuropeptides. A variety of these allatostatins have been previously described and are suitable for use herein. As mentioned, the allatostatin polypeptide to which the hydrophobic moiety is attached should include at least an active C-terminal portion containing the C-terminal pentapeptide $Xaa_3\text{-}X_1\text{-}Phe\text{-}Gly\text{-}X_2\text{-}NH_2$, and may encompass the entire native allatostatin polypeptide. However, the polypeptide should not be so large as to lose the hydrophobic character introduced by the hydrophobic moiety. Thus, without being limited thereto, the size of the polypeptide (including the above-mentioned C-terminal pentapeptide) is usually less than or equal to about 20 amino acids, particularly less than or equal to about 10 to 12 amino acids. As described in the first embodiment, the aromatic ring of the Tyr or Phe amino acid ($Xaa_3$) may again be replaced by a carborane moiety (i.e. substituting carboranyl alanine for the Phe or Tyr).

The above-mentioned hydrophobic aromatic acids or amines or the aliphatic fatty acids may be conjugated to the allatostatin peptide directly or through an optional spacer. Use of the spacer is preferred however, to minimize any steric hindrance of the active polypeptide portion of the compound by the hydrophobic moiety and inhibition of receptor binding. The structure of the spacer will vary with the particular hydrophobic group. Without being limited thereto, when the hydrophobic moiety is an aromatic acid or an aliphatic fatty acid, preferred spacers may be non-polar hydrocarbons having a free amino group and free carboxyl group, or relatively non-polar or uncharged a-amino acids, such as Ala, Ala—Ala dimer, or Gly. When using an aromatic amine as the hydrophobic moiety, preferred spacers are hydrocarbon diacids, such as succinic acid. Other specific spacers may be readily determined by the practitioner skilled in the art.

In summary, in accordance with the structure shown in Formula (I), the structure of R for the second embodiment may be shown as:

$$R_1\text{-}Lm\text{-}X_4\text{-}R_2\text{-}X_3\text{-} \quad\quad (IV)$$

where $R_1$ is the above-mentioned hydrophobic moiety, L is the spacer, m is 0 or 1, $X_4$ is a bond or Arg, and $X_3$ is Tyr, Phe or carboranyl alanine. The group $R_2$ may be a bond, or an amino acid or polypeptide which is naturally contiguous to the C-terminal pentapeptide $Xaa_3\text{-}X_1\text{-}Phe\text{-}Gly\text{-}X_2\text{-}NH_2$. Without being limited thereto, specific examples of suitable $R_2$ moieties include:

-Leu-,
-Ala-Tyr-Ser-Tyr-Val-Ser-Glu-Tyr-Lys-Arg-Leu-Pro-Val-, (SEQ ID NO: 1)
-Ser-Lys-Met-,
-Asp-Gly-Arg-Met-(SEQ ID NO: 2),
-Asp-Arg-Leu-,
-Ala-Arg-Pro-,
-Ala-Pro-Ser-Gly-Ala-Gln-Arg-Leu-(SEQ ID NO: 3),
-Gly-Gly-Ser-Leu-(SEQ ID NO: 4),
-Gly-Asp-Gly-Arg-Leu-(SEQ ID NO: 5),
-Pro-Val-Asn-Ser-Gly-Arg-Ser-Ser-Gly-Ser-Arg-(SEQ ID NO: 6),
-Tyr-Pro-Gln-Glu-His-Arg-(SEQ ID NO: 7), and
-Pro-.

In a third embodiment for the preparation of allatostatin analogs capable of penetrating the insect cuticle, the aromatic ring of the Tyr or Phe amino acid ($Xaa_3$) is replaced by a carborane moiety. While this modification is the same as described in the first and second embodiments (substituting carboranyl alanine for the Phe or Tyr), this embodiment does not require the use of additional hydrophobic groups as described in the earlier embodiments. The resultant pseudopentapeptide analog may include an optional amino acid, Arg, conjugated to the free amine group of the carboranyl alanine.

In summary, referring to Formula 1, in this third embodiment the structure of R may be shown as:

R$_3$-carboranyl alanine-wherein R$_3$ is H or Arg.

In accordance with a further embodiment, the invention also encompasses the preparation of allatostatin analogs which are resistant to degradation by insect peptidases while still retaining biological activity. These analogs may be prepared by substituting selected sterically hindered amino acids and/or aromatic acids for the second, third and/or fifth amino acids of the allatostatins or active C-terminal portions thereof containing the C-terminal pentapeptide Xaa$_3$-X$_1$-Phe-Gly-X$_2$-NH$_2$ (Xaa$_3$, X$_1$, and X$_2$ being as described above).

The substituted amino acids or aromatic acids incorporated into the pentapeptide must possess sufficient bulk as to sterically hinder cleavage of the analog by peptidases in the target insect, yet substantially retain the secondary structure and active conformation of the native allatostatin pentapeptide necessary for biological activity. In this embodiment, the Phe of the native C-terminal pentapeptide is replaced with 2-amino-indane-carboxylic acid (Aic), and/or the Gly is replaced with either cyclopropyl alanine (Cpa) or cyclobutyl alanine (Cba). Alternatively, both the Phe and Gly may be replaced with 1,4-benzodiazepine (Bzd). These substitutions may be incorporated into the complete allatostatins or into active C-terminal portions thereof which contain the C-terminal pentapeptide.

All of the Bzd, Cpa, and Aic containing analogs retain significant biological activity and increased resistance to peptidase degradation. The Aic containing analogs in particular exhibit biological activity comparable to the native allatostatin C-terminal pentapeptide. Each of the Aic, Cpa, and one of the diastereomers of the Bzd containing analogs exhibit inhibition of JH biosynthesis in the cockroach in the physiological ($\mu$M or lower) range. Interestingly, rather than inhibiting JH biosynthesis, the other diastereomer of the Bzd containing analog actually stimulates JH biosynthesis in the cockroach. Despite these apparent differences, all of the analogs are effective for insect control as described hereinbelow. Although these analogs exhibit resistance to degradation by hemolymph peptidases as well as membrane bound peptidases at their primary cleavage site, between Gly and Leu-NH$_2$ in the native pentapeptide, they are still susceptible to degradation by the membrane bound peptidases at their secondary cleavage site near the N-terminal end of the pentapeptide.

In contrast to the allatostatin pentapeptide analogs incorporating sterically hindered amino acids at the second or third amino acids, analogs prepared by substitution of hydrocinnamic acid (Hca) or hydroxycinnamic acid (Hhca or hydroxyphenyl propionic acid) for the N-terminal Xaa$_3$ amino acid (Tyr or Phe) of the C-terminal allatostatin pentapeptide, exhibit significantly increased resistance to degradation by membrane bound peptidases near the N-terminus of the molecule. These analogs also retain significant biological activity. The Hca or Hhca replace the N terminal Tyr or Phe, capping the peptide and effectively removing the N-terminal cleavage sites of the membrane bound peptidases within the native pentapeptide, and also blocking the N-terminal primary cleavage sites of the hemolymph enzymes.

While the above-described Cpa, Aic, Bzd, and Hca (or Hhca) substitutions may be incorporated into the analog individually, in the preferred embodiment, optimal resistance to insect peptidases is achieved by substitution of each of the second, third and fifth amino acids as described. Thus, in the preferred embodiment, the analogs will incorporate both the substitution of an Hca or Hhca for Xaa$_3$, and substitution of the Phe or Gly with Aic or Cpa, respectively, or substituting both Phe and Gly with Aic-Cpa or with Bzd.

Figure 2:
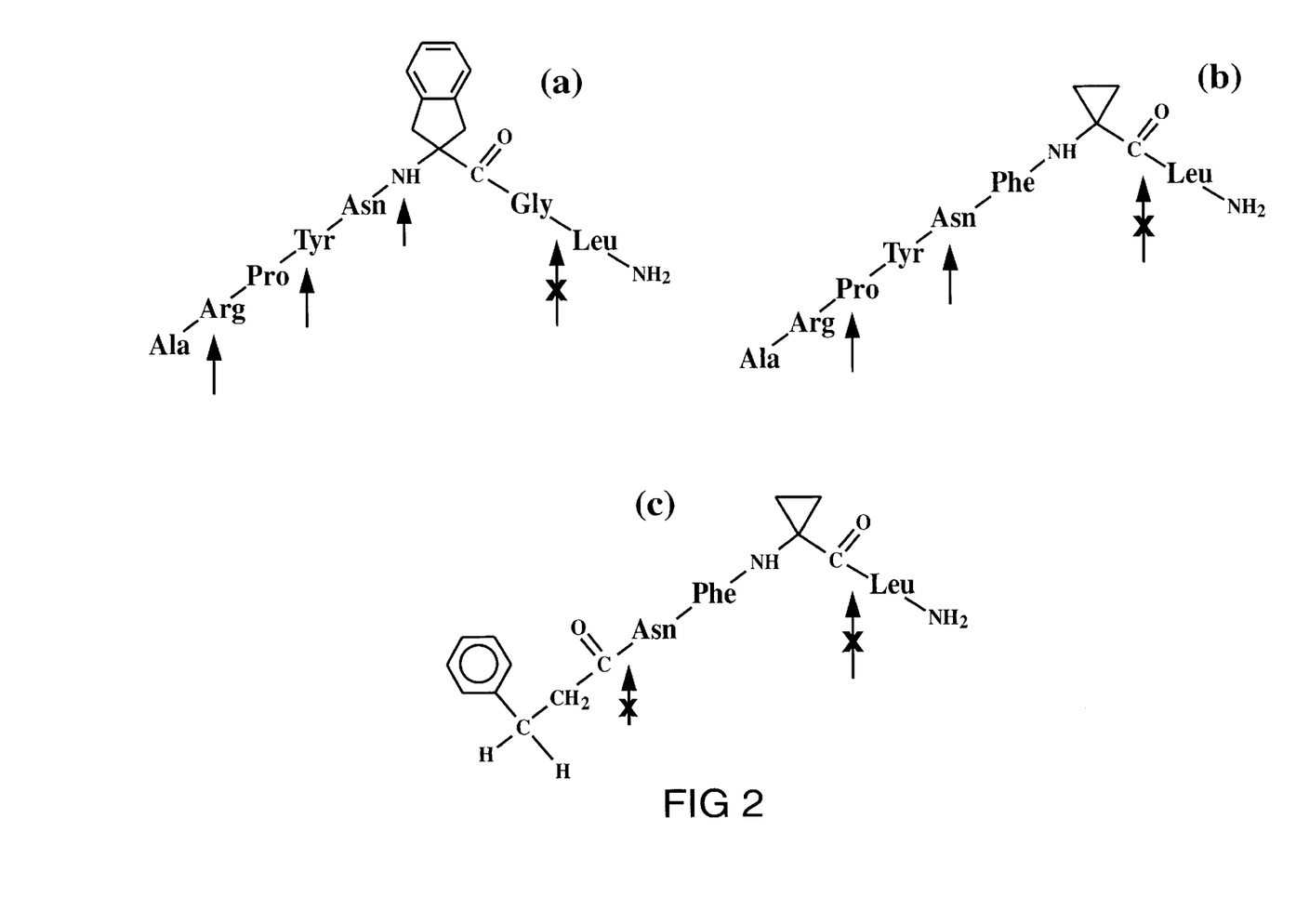
FIGS. 2(a)–(c) show the structures of peptidase resistant allatostatin analogs containing sterically hindered, restricted conformation components: a) indane ring (Aic) analog 396-1, top left; b) cyclopropyl ring (Cpa) analog 397-2, top right; and c) cyclopropyl ring (Cpa) analog with a hydrocinnamic acid (Hca) 'cap' replacement for Phe [AST(b)φ2], bottom center. Upward arrows denote cleavage sites of tissue-bound peptidases in the cockroach. The large upward arrows with a cross over them, indicate a peptidase cleavage site that is blocked by the presence of the sterically hindered components and/or presence of the hydrocinnamic acid cap.
Figure 3:
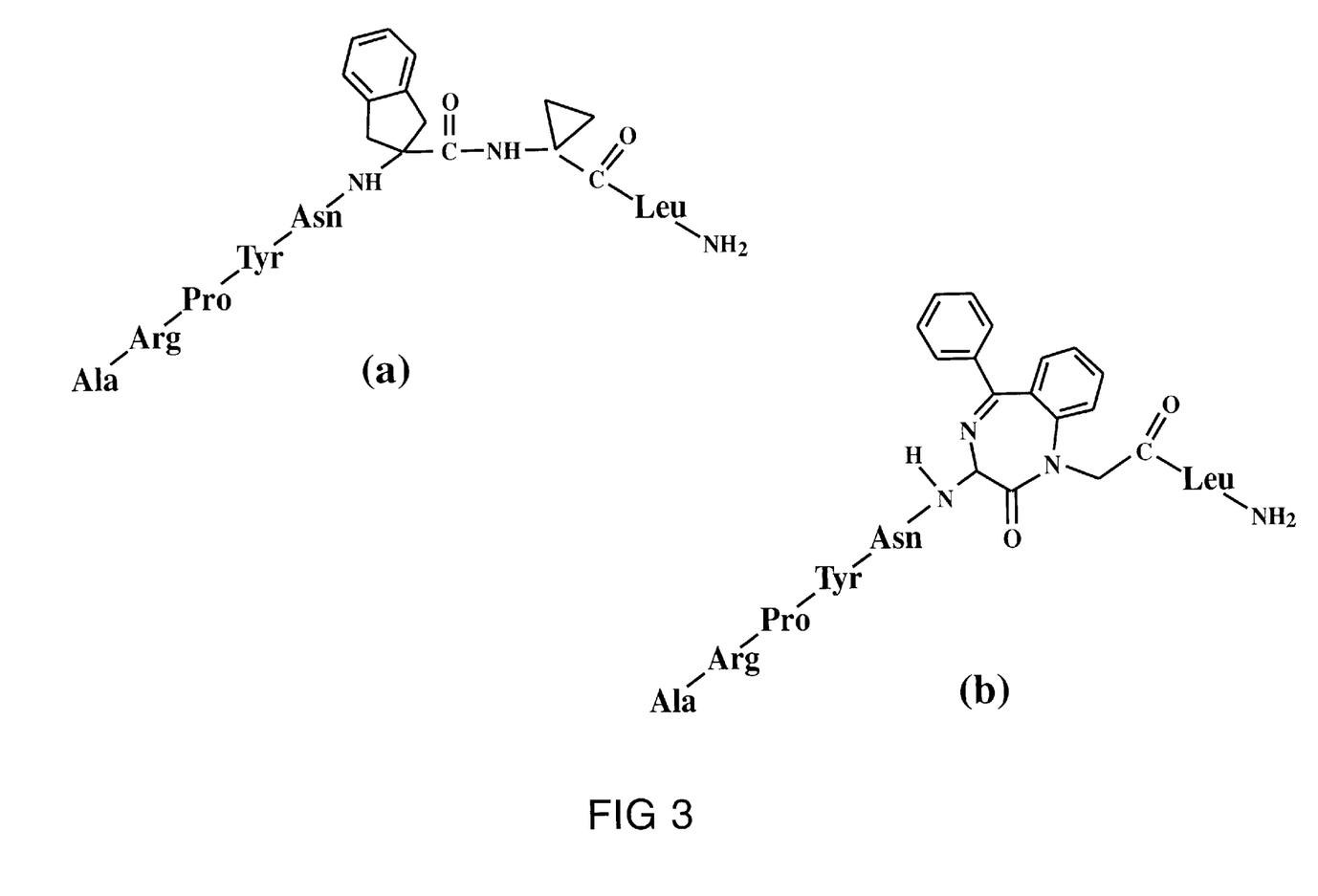

In review, the peptidase-resistant allatostatin analogs of this invention may be generally shown by the formula:

R'-R-X$_1$-X$_a$-X$_b$-X$_2$-NH$_2$  (V)

wherein X$_1$ and X$_2$ are as described above in formula I. R' may be Phe, Tyr, a hydrocinnamyl group, a hydroxyhydrocinnamic acyl group, or a polypeptide group which may be all or a portion of an allatostatin neuropeptide which is naturally contiguous to the C terminal tetrapeptide X$_1$-Phe-Gly-X$_2$-NH$_2$. X$_a$-X$_b$ may be any of Phe-Caa, Aic-Gly, Aic-Caa, or Bzd, wherein Caa is a cycloalkyl alanine selected from cylcopropyl alanine or cyclobutyl alanine, Aic is a 2-amino-indane-2-carboxyl group, and Bzd is a 1,4-benzodiazepine group. Detailed structures of peptidase resistant analogs representative of this embodiment are shown in FIGS. 2 and 3. The peptidase resistant analogs of this invention are also described in Nachman et al. (1997, Active Conformation and Peptidase Resistance of Conformationally Restricted Analogues of the Insect Allatostatin Neuropeptide Family, IN: Kawashima and Kikuyama, Advances in Comparative Endocrinology, Bologna, Italy: Monduzzi Editore, pp. 1353–1359), Garside et al. (1997, Catabolism of Insect Neuropeptides: Allatostatin as Models for Peptidomimetic Design, IN: Kawashima and Kikuyama, Advances in Comparative Endocrinology, Bologna, Italy: Monduzzi Editore, pp. 169–173), and (1998, Bioorganic & Medicinal Chemistry, 6:1379–1388) the contents of each of which are incorporated by reference herein.

Although the preparation and use of analogs capable of penetrating the insect cuticle and analogs resistant to peptidase degradation may be practiced separately, it is also understood that analogs may be prepared which incorporate the modifications of each embodiment. Thus in a particularly preferred embodiment, a hydrophobic moiety is conjugated to the allatostatin peptide or a bioactive portion thereof, while one or both of Aic or Cpa are substituted for the Phe or Gly, respectively, or Bzd is substituted for both Phe and Gly, within the C-terminal pentapeptide core.

The analogs of this last embodiment may be shown by the formula:

R-X$_1$-X$_a$-X$_b$-X$_2$-NH$_2$  (VI)

wherein R, X$_1$, and X$_2$ are as described in formula I, and X$_a$-X$_b$ are as described in formula V hereinabove.

The peptides and pseudopeptide analogs of this invention may be synthesized by any suitable method, such as exclusively solid-phase techniques, partial solid-phase techniques, fragment condensation, or classical solution addition. The groups or amino acids of the compounds of the invention, including the R groups, are typically joined to adjacent groups through amide linkages. The peptides may also be synthesized by recently developed recombinant DNA techniques which may be utilized for large-scale use.

Synthesis by the use of recombinant DNA techniques, for the purpose of this application, should be understood to include the suitable employment of structural genes coding for the sequence as specified hereinafter. The synthetic peptides may also be obtained by transforming a microorganism using an expression vector including a promoter or operator, or both, together with such structural genes and causing such transformed microorganisms to express the peptide.

As stated above, the compounds of formulas I-VI can be synthesized by methods well known to those skilled in the art of peptide synthesis, e.g., solution phase synthesis [see Finn and Hoffman, In "Proteins," Vol. 2, 3rd Ed., H. Neurath and R. L. Hill (eds.), Academic Press, New York, pp. 105–253 (1976)], or solid phase synthesis [see Barany and Merrifield, In "The Peptides," Vol. 2, E. Gross and J. Meienhofer (eds.), Academic Press, New York, pp. 3–284 (1979)], or stepwise solid phase synthesis as reported by Merrifield [J. Am. Chem. Soc. 85: 2149–2154 (1963)], the contents of each of which are incorporated herein by reference. In the preferred embodiment, the allatostatin polypeptides and the analogs may be synthesized using the same solid phase techniques described by Nachman et al. (1995, Reg. Peptides, 57:359–370) or Christensen et al. (1991, Proc. Natl. Acad. Sci., USA, 88:4971–4975), the contents of each of which are incorporated by reference herein. Cbe or 2-o-carboranylpropanoic acid may be synthesized according to previously described procedures (Radel and Kahl, 1993, Amino Acids, 5:170, the contents of which are incorporated by reference herein). The hydrophobic moieties may be incorporated into the analogs using the techniques described in Nachman et al. for the preparation of pyrokinin analogs (U.S. Pat. No. 5,795,857, issued Aug. 18, 1998, the contents of which are incorporated by reference herein).

The pseudopeptide analogs of formulas I-VI mimic the biological activity of the naturally occurring allatostatin neuropeptides and have demonstrated the ability to disrupt or alter physiological processes following application to an insect. In a preferred embodiment, with one exception, the pseudopeptide analogs of each of the embodiments are effective for inhibiting juvenile hormone production in cockroaches, thereby causing infertility in adults. Furthermore, inhibition of juvenile hormone production in immature insects causes precocious adult development resulting in sexual dysfunction. As noted above, rather than inhibiting juvenile hormone biosynthesis, one of the diastereomers of the Bzd containing analogs stimulates production of the hormone in cockroaches. Application of these analogs to immature insects may prevent or inhibit their development to adults. The compounds appear to be particularly suited for control of insects of the order Dictyoptera and Orthoptera, especially cockroaches and locusts.

As a practical matter it is anticipated that compositions of the pseudopeptide analogs would be prepared by formulating the compounds with an agriculturally acceptable inert carrier, particularly a solvent suitable for topical applications. Although a variety of solvents may be used, water is preferred. The compounds may also be formulated with solid inert carriers such as talc, clay or vermiculite, or incorporated into conventional controlled release microparticles or microcapsules. In addition, the analogs may be optionally formulated in combination with conventional insect attractants, baits, or other chemical or biological insecticides.

The allatostatin analogs of this invention may be applied directly to the target insects (i.e., larvae, pupae and/or adults), or to the locus of the insects. Because the compounds incorporating hydrophobic moieties will penetrate the insect cuticle, they are preferably administered topically, such as by direct spraying on the insect or a substrate which is likely to be contacted by the insect. Alternatively, the compounds may also be administered either subcutaneously, percutaneously, or orally. When they are to be ingested, they should be applied with their carrier to the insect diet. The compounds are administered in an amount effective to induce the desired response as determined by routine testing. For example, where the desired effect is the inhibition of juvenile hormone biosynthesis, an "effective amount" is defined to mean those quantities which will result in a significant decrease in juvenile hormone production in a test group as compared to an untreated control. Similarly, where the ultimate response is pest mortality, an "effective amount" is defined as those quantities which will result in a significant mortality rate in a test group as compared to an untreated control. The actual effective amount will of course vary with the specific compound, the target insect and its stage of development, the application technique, the desired effect, and the duration of the effect, and may be readily determined by the practitioner skilled in the art. When determining effective amounts, it is understood that these analogs need not be as potent as the natural allatostatin peptide to disrupt physiological processes such as juvenile hormone biosynthesis, because their effects can be exerted over a considerable time, as a consequence of their resistance to peptidase degradation. Without being limited thereto, it is envisioned that when administering the analogs by ingestion, effective inhibition of juvenile hormone biosynthesis may be achieved using concentrations of between about 100–500 picomoles/insect. When the compounds are to be topically applied, the effective amounts may be significantly higher.

It is envisioned that the compounds encompassed herein may be effective for controlling a variety of insects. Without being limited thereto, pests of particular interest are agronomically or commercially important insects, especially cockroaches and locusts.

The following examples are intended only to further illustrate the invention and are not intended to limit the scope of the invention which is defined by the claims.

EXAMPLE 1

Materials and Methods

Cuticle Preparation

Adults of the American cockroach were obtained from colonies at our facility (CMAVE). Animals, anesthetized by submersion in $H_2O$ for 30 min, were pinned ventral side up in a wax dissecting dish flooded with water. Lateral incisions along the margins of the abdominal sternites were made between segments 1–7. The epidermal layers including the cuticle and epidermal cells were lifted up and associated tissue was cleared using forceps prior to removal. The epidermal tissue was placed cell side up on a microscope slide and the cells were scraped from the cuticle using a glass cover slip. To further clean the cuticle of cellular debris the tissue was floated, cell side down, in a beaker containing $H_2O$ and subjected to sonication in a water bath at 30° C. for 30 min. The cuticle strips were then washed 3× in clean water. Pieces of cuticle, ca. 0.4 $cm^2$, composed of individual sternites without associated intersegmental membranes were then dissected away from remaining cuticle.

Incubation of Cuticle

Incubation of cuticle was accomplished using the wells of ELISA plates (Corning, 96 well Easy Wash). Prior to use the wells of the plates were blocked to minimize adsorption of analogs to the wells by filling with a 1% gelatin in 10 mM sodium phosphate buffer containing 150 mM NaCl (pH 7.25) (PBS) and incubating at 35° C. for 1.5 h. After blocking, the plates were washed with PBS-Tween and followed by three washes with $H_2O$. The wells of the plates were filled with 300 µl of $H_2O$ and pieces of cuticle were floated, cell side down, in the wells. The 9-fluoreneacetic acid pentapeptide analog (0.5 nmol) was applied to the center of the cuticle pieces in a 0.5 µl drop of $H_2O$ using a Hamilton 10 µl syringe fitted with a fused silica needle (0.17 mm OD) and held in a Brinkmann micromanipulator. All applications and transfers were made using a microscope and the preparations were observed for 5 min after application of the analogs to insure that drops did not slide off the cuticle. Data from wells in which the drops slid off the cuticle were not considered for analysis. Lids were applied to the plates after the drops of water containing the analogs dried (ca. 5 min after application) and the plates were placed on an orbital shaker operated at 80 rpm. At this speed no water contacted the upper surface of the cuticle. One h after application of the analogs we carefully transferred the cuticle to new wells containing 300 μl of H$_2$O and incubation was continued. Cuticle was subsequently transferred to new wells at intervals after application of the analog. After incubation, 100 pmol of internal standard were added to the wells. The contents of the wells were mixed by pumping the contents in and out of a micro pipette several times and then transferred to a 1.5 ml microfuge tube. The wells were extracted two additional times by addition of 350 μl of water and the extracts combined prior to concentration to apparent dryness using a SpeedVac concentrator.

Dried samples were reconstituted in 35% acetonitrile (MeCN) (Burdick and Jackson) prior to analysis. Reversed phase liquid chromatographic analysis (RPLC) was accomplished using a LDC Biochrome quaternary gradient pump and LDC Spectro Monitor 3200 UV detector set at 210 nm and interfaced to a Nelson Analytical 3000 data acquisition and analysis system. A Macrosphere 300 C18 reversed phase column (250 mm×2.1 mm id, 5 μm, Alltech) was used for all separations. Solvents used for all separations were H$_2$O and MeCN each containing 0.1% TFA as the ion pair reagent. Samples were injected onto the column using a Rheodyne 7125 injector (100 μl loop) in 35% MeCN. The column was eluted after a 5 min equilibration period using a linear gradient from 35%–75% MeCN over 90 min at a flow rate of 0.25 ml/min. Analysis of equimolar amounts of analogs indicated that the compounds had different detector responses when analyzed with the UV detector set at 210 nm. Therefore, all values were corrected to reflect the differential detector response for the analogs. Data acquired from analyses were reduced and analyzed using NCSS 97 software using regression analysis and T-Tests.

Radiochemical Assay

Rates of JH release were determined by the in vitro radiochemical method of Feyereisen and Tobe (Anal. Biochem., 111:372–375, 1981) and as modified by Tobe and Clarke (Tobe and Clarke, Insect Biochem., 15:175–179, 1985). The incorporation of L[$^{14}$C-S-methyl]-methionine (50 μM, specific radioactivity 1.48–2.03 GBq/mmol from New England Nuclear or Amersham) into JH III at its penultimate step of biosynthesis by CA incubated in 50 μl TC 199 (GIBCO, 1.3 mM Ca$^{2+}$, 2% Ficoll, methionine-free) was used to quantify JH release. Animals were anaesthetized on ice prior to dissection. Corpora allata were dissected directly into non-radioactive medium (only animals with oviposited basal oocytes were used for assay). Samples were dried with nitrogen and resuspended in 10 μl 1N HCl. Radioactive medium was added and neutralized with 10 μl NaOH. Individual CA were transferred from non-radioactive medium to radioactive medium and were incubated for 3 h. The amount of inhibition was expressed as the percent reduction from the untreated rate: [1−(treated rate/untreated rate)]×100%. Each value represents replicate incubations of a minimum of 8 tests.

Controls

All experiments were run with appropriate controls (Dip-AST5 incubated for 120 min with no membrane preparations added). If the identical amount of AST was incubated under the same conditions with saline alone, the size of the HPLC-detected peak (U.V. 214 nm) remained constant over a 120 min period. The addition of 200 μl of 30% aqueous TFA completely inactivated the enzymes in the membrane preparations and in intact CA.

Results

Figure 1:
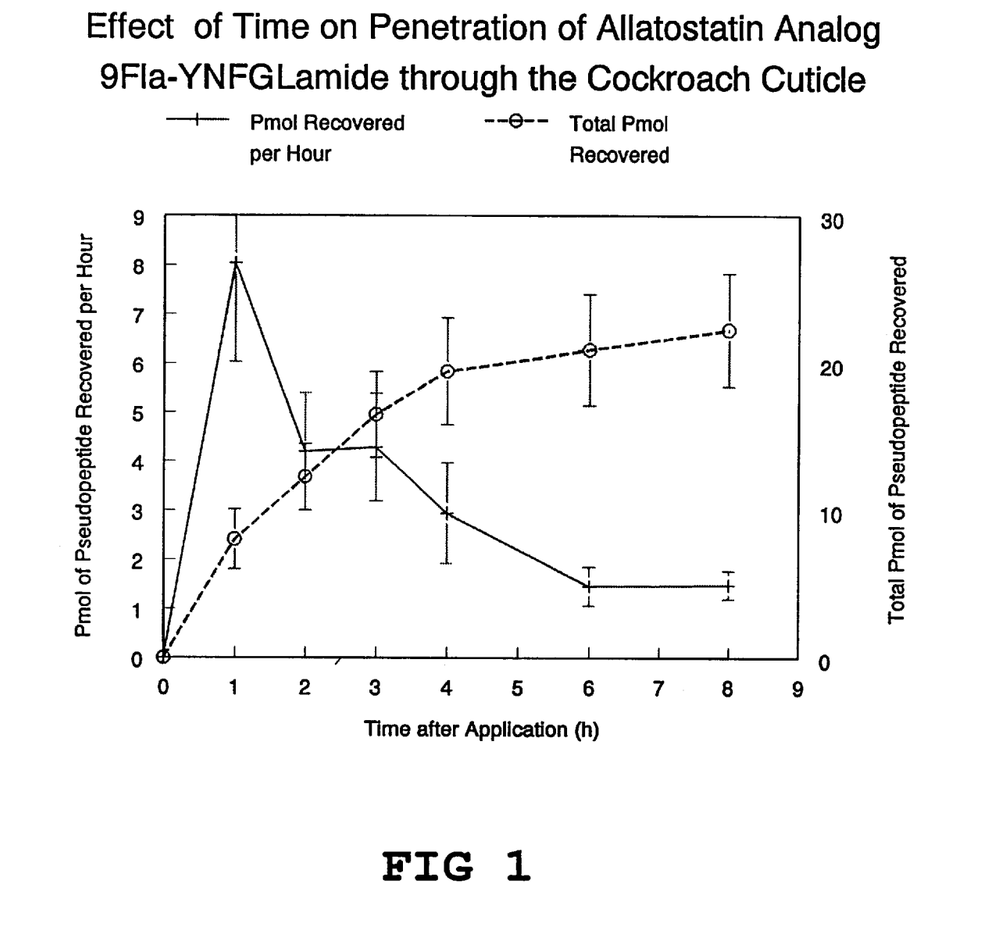
FIG. 1 shows the effect of time on the penetration of the 9-fluoreneacetic acid pentapeptide analog of Example 1 through the cuticle of the cockroach.

Analysis of samples obtained when using cockroach cuticle indicated that the analog penetrated the cuticle effectively (FIG. 1). The total amount of each of the analogs recovered over time increased in a logarithmic fashion (r=0.988, n=7/sample interval) over the test period. Although the amount released per hour declined significantly during the first six hours after application the release rate stabilized after six hours to about 1.5 pmol/h. The logarithmic rates of release of the three analogs through the cuticle of the cockroach demonstrated that the cuticle was acting as a slow release matrix for the analog. The initial rapid rates of release indicated that the cuticle at the region of application was saturated with pseudopeptide and that the analog was penetrating at its maximal rate. As time progressed, analog was absorbed and distributed more evenly in the cuticle surrounding the point of application. Therefore, equilibrium was established throughout the cuticle so that the rate of release was reduced and declined slowly in a linear fashion.

The activity of the 9-fluoreneacetic acid pentapeptide analog (analog 525) was $2.6×10^{-7}$ M (ED$_{50}$ or EC$_{50}$). In another assay, the activity of the carborane containing analog, carboranyl propanoic acid-Ser-Phe-Gly-Leu-NH$_2$, was $6.442×10^{-10}$ M (ED$_{50}$)

EXAMPLE 2

Materials and Methods

Allatostatin Analog Synthesis

The allatostatin analogs 396-1 (Ala-Arg-Pro-Tyr-Asn-Aic-Gly-Leu-NH$_2$, Aic=2-amino-indane-2-carboxyl-) and 397-2 (Ala-Arg-Pro-Tyr-Asn-Phe-Cpa-Leu-NH$_2$, Cpa=cyclopropylAla) were synthesized as previously described Nachman et al. (1997, 1998, ibid). The pseudopeptide allatostatin analog AST(b)φ2 (Hca-Asn-Phe-Cpa-Leu-NH$_2$, Hca=Hydrocinnamyl- and Cpa=cyclopropylAla-) was synthesized utilizing FMOC protection chemistry on MBHA resin (0.97 meq/gm substitution; Advanced Chemtech, Louisville, Ky.). Coupling reagents used for the majority of the amino acid condensations were 1 eq. of 1,3-diisopropyl carbodiimide/1-hydroxy-7-azabenzotriazole (HOAt) mixture in dimethylsulfoxide for 2 h according to previously described procedures (Nachman et al., Peptides, 18:53–57, 1997). However, for coupling of the Cpa residue and the residue immediately following Cpa to the peptide-resin complex the reagent used was 1 eq. [O-(7-azabenzotiazol-1-yl)-1,1,3,3-tetramethyluronium hexafluorophosphate] (HATU)(PerSeptive Biosystems, Marlborough, Mass.) with 2 eq. N,N-diisopropylethylamine in dimethylsulfoxide for 4 h. Removal of the N-terminal FMOC group from the Cpa was accomplished with 20% piperidine in dichloromethane for 1 h rather than the 30 min used for the other residues. The peptide was cleaved from the resin with HF according to previously described conditions (Nachman et al., Peptide Res., 2:171–177, 1989). The crude product was purified on a Waters C18 Sep Pak cartridge followed by a Delta Pak C18 reverse phase column on a Waters model 510 HPLC controlled with a Millenium 2010 chromatography manager system (Waters, Milford, Mass.) with detection at 214 nm at ambient temperature. Solvent A=0.1% aqueous trifluoroacetic acid (TFA); solvent B=80% aqueous acetonitrile containing 0.1% TFA. Conditions: Initial solvent consisting of 20% B was followed by Waters linear program 6—100% B over 40 min; flow rate 2 ml/min. Retention time Hca-Asn-Phe-Cpa-Leu-NH$_2$): 15.0 min. The pure pseudopeptide analog was analyzed and quantified by amino acid analysis under previously described conditions, revealing the following analysis: F(1.0), L(1.0) and N(0.9). A fast atom bombardment (FAB) mass spectrum was obtained by adding 10 g of pseudopeptide sample to glycerol (1.5 μl) on a copper probe, followed by bombardment with 8 kV Xe atoms on a Kratos MS-50 mass spectrometer (Kratos, Manchester, UK). The structural identity and a measure of the purity of the pseudopeptide was confirmed by the presence of the following molecular ion (MH$^+$): Hca-Asn-Phe-Cpa-Leu-NH$_2$, 607.4 (Calc. MH$^+$: 607.32).

Animals

D. punctata females mate almost immediately following emergence. Therefore, newly emerged, mated females were transferred each day from the stock culture to an incubator and kept at 27±1° C. The relative humidity was approximately 50% with a 12 hour light:dark cycle. Insects were reared on Purina Lab Chow and water. Mating was confirmed by the presence of a spermatophore. Basal oocyte length was also measured (day 5=1.44–1.68 mm). Only day 5 mated females were utilized for the degradation studies. Day 7 mated females (only with oviposited basal oocytes) were the source of corpora allata for analysis of JH biosynthesis.

Solid Phase Extraction

Preparation

Pasteur pipettes were used to make C$_{18}$ reversed-phase columns. A glass bead was placed in the bottom of each Pasteur pipette and approximately 200 mg 125 Å C$_{18}$ bulk packing material was added. Glass wool was placed over the top of the packing material to hold it in place.

Procedure

Each column was washed with 1.5 ml of 0.1% BSA in 0.1% aqueous TFA, followed by 1.5 ml of 40% acetonitrile in 0.1% TFA and finally, 1.5 ml of 0.1% aqueous TFA. Samples were diluted in 0.2 ml 0.1% aqueous TFA and applied to column. Eluant was reapplied to the column 2×. The column was washed with 1.5 ml 0.1% aqueous TFA followed by 17% acetonitrile in 0.1% aqueous TFA. The allatostatins and their metabolites were eluted with 0.5 ml 40% acetonitrile in 0.1% aqueous TFA into 12 mm×75 mm culture tubes and were dried with a Speed-Vac.

Protein Assay

Protein content of membrane preparations was determined by the method of Bradford (Bradford, Anal. Biochem., 72:248–254, 1976) using BSA as standard. The average of three separate determinations was used.

Allatostatin Degradation Assay

Tissue Collection

Day 5 mated female D. punctata were anaesthetized on ice before dissection. Following dissection, tissues were stored in saline (0.9% NaCl pH 7.0–7.2 or cockroach saline; NaCl 150 μM, KCl 12 μM, CaCl$_2$.6 H$_2$O 10 μM, MgCl$_2$. 6 H$_2$O 3 μM, glucose 40 μM, HEPES 10 μM at pH 7.2–7.4) on ice. Tissues were cleaned of fat body and trachea and guts were cleaned. Midgut peritrophic membrane was removed, midguts cut open, the guts gently pulled through forceps and then washed 3×. Tissues were stored at −70° C. until sufficient material was collected.

Membrane preparation

Tissues were pooled and homogenized in saline on ice in microcentrifuge tubes (2.5 ml) for 2 min with an Omni hand held homogenizer. Homogenates were centrifuged at 1000 g for ten min at 4° C. to remove cellular debris. The pellet was discarded. Supernatant was subsequently centrifuged at 30,000 g for 30 min. Pellet (crude membrane preparation) was washed three times in homogenization buffer and resuspended in saline using the Omni homogenizer.

Hemolymph preparation

Hemolymph was collected following the method of King and Tobe (Insect Biochem., 18:793–805, 1988). Hemolymph was diluted 100× with saline.

Assay

Crude membrane preparation or hemolymph was aliquoted into 1.5 ml microcentrifuge tubes for in vitro assay. Dip-AST5 (6 μM) or analog was added to each assay tube from a 1 mM stock solution. Total incubation volume was 500 μl. Tubes were placed on a shaker at room temp for the duration of the incubation time. Incubations were terminated by the addition of 200 μl 30% aqueous TFA. Samples were centrifuged at 10,000 g and the supernatant was applied to a C$_{18}$ solid phase extraction column. None of the potential, synthetic Dip-AST5 metabolites are lost (unpublished data). The 17–40% acetonitrile fraction was concentrated with a Speed-Vac apparatus and held at −70° C. until HPLC analysis. Samples were diluted in 0.5 ml 0.1% aqueous TFA, filtered through 0.2 μm micro-spin filters and injected onto the HPLC column. Separation of allatostatins and their catabolites, or analogs and their catabolites, was performed using reversed-phase HPLC (see HPLC methods). When available, retention times of synthetic metabolites were used as a reference to identify endogenous metabolites. Dip-AST5 fragments were synthesized by the Institute for Biosciences and Technology, Dept. of Entomology, Texas A & M University. Dip-ASTs were synthesized by the Core Facility of Insect Biotech Canada (Department of Biochemistry, Queen's University) or obtained from Sigma Chemical Co., St. Louis, Mo. 63178 USA. The identity of fragments resulting from peptidase degradation was also confirmed by FAB mass spectrometry by adding samples in a glycerol medium (1.5 μl) onto a copper probe, followed by bombardment with 8 kV Xe atoms on a Kratos MS-50 mass spectrometer (Kratos, Manchester, UK).

HPLC

Degradation experiments were analyzed by RP-HPLC using a 220×4.6 mm Brownlee Phenyl column (5 μm) on a Spectra-Physics chromatography system with a Spectra-Physics Chromjet integrator and a Spectra-Physics 8490 detector. Following a 5 min wash with 15% acetonitrile in 0.1% aqueous TFA, a linear gradient of acetonitrile (15–37.5% in 50 min; 37.5–65% in 5 min) at a flow rate of 0.5 ml/min was used to elute peptides and analogs. Fractions (0.5 ml) were collected each minute during the gradient run.

Radiochemical Assay

Radiochemical assays were conducted as described in Example 1.

Controls

Controls were prepared and conducted as described in Example 1.

Results

In analog 396-1 (Ala-Arg-Pro-Tyr-Asn-Aic-Gly-Leu-NH$_2$), the Phe residue was replaced with an indane ring system (abbreviated Aic =2-Amino-indane-2-carboxyl-; see FIG. 1) which preserved the presence of the side chain phenyl ring, a structural feature critical for biological activity (Hayes et al., ibid). In a second analog (397-2: Ala-Arg-Pro-Tyr-Asn-Phe-Cpa-Leu-NH$_2$), the Gly residue was replaced with a cyclopropyl ring system (abbreviated Cpa= cyclopropylAla-, see FIG. 2). Molecular dynamics analyses, incorporating distance and angle constraints obtained from NMR spectroscopy, were conducted separately for each of the analogs of the series. All demonstrated a preference for a very similar low energy turn over the four C-terminal residues.

Both allatostatin analogs 396-1 and 397-2 retained significant bioactivity (Table 2); specifically, 396-1 has an IC$_{50}$=2.12 nM which compares favorably to Dip-AST5 which has an IC$_{50}$=3.1 nM. Patterns of peptidase hydrolysis by hemolymph enzymes for analogs 396-1 and 397-2 indicate that the analogs were targeted at peptide bonds outside of the active core region. The analogs were cleaved near the N-terminus, initially at Arg-Pro, followed by cleavage at Pro-Tyr. These sites of cleavage are directly comparable to the sites of cleavage in the natural peptide Dip-AST5 by soluble hemolymph enzymes (Arg-Leu and Leu-Tyr) (Garside et al., Peptides, 18:17–25, 1997).

Surprisingly, these analogs showed little resistance to degradation by enzymes in crude membrane preparations.

Whereas the modifications successfully prevented truncation of the C-terminal Leu-NH$_2$, both analogs were still degraded at secondary cleavage sites near the N-terminus, similar to those observed following incubation of allatostatins with hemolymph enzymes. Membrane-bound (brain and midgut) peptidases cleaved 396-1 first at Ala-Arg, followed by cleavage at Pro-Tyr and then at Asn-Aic yielding the C-terminal tripeptide (Aic-Gly-Leu-NH$_2$). Analog 397-2 was initially cleaved at Arg-Pro followed by cleavage at Tyr-Asn. Interestingly, we found no evidence of aminopeptidase removal of the N-terminal Ala in analog 397-2.

Figure 4:
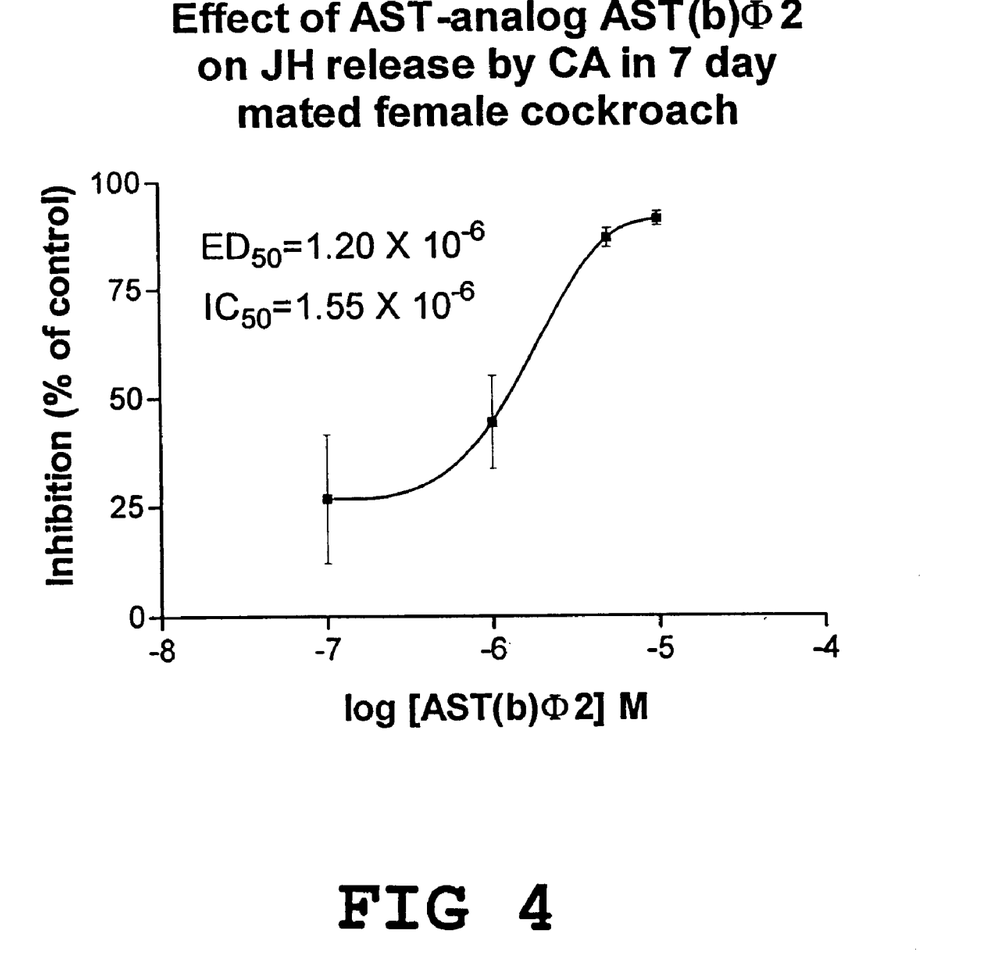
FIG. 4 shows the dose-response curve for inhibition of in vitro juvenile hormone JH biosynthesis in corpora allata of the cockroach Diploptera punctata by allatostatin analog AST(b)φ2 in Example 2. Each point for analog treatment represents the mean of 14–16 measurements +/− the standard error of the mean.

Since cleavage of analogs 396-1 and 397-2 occurred near the N-terminus, we synthesized analog AST(b)φ2 (FIG. 1), which retained the cyclopropyl ring system of 397-2 at the C-terminus and also incorporated an unnatural, non-amino acid group, hydrocinnamic acid, at the N-terminus. The hydrocinnamic acid group replaces the critical N-terminal Tyr, thereby effectively removing both cleavage sites suggested from the incubation of Dip-ASTs with hemolymph enzymes. This also effectively removed the sites targeted by membrane-bound enzymes in analog 397-2. The hydrocinnamic acid moiety lacks the phenolic OH group and N-terminal amino group of the Tyr residue. This analog exhibited extreme resistance to degradation by enzymes in hemolymph and in crude membrane preparations of brain and midgut (Table 1). Assay of AST(b)φ2 for inhibition of JH biosynthesis indicates that it does retain significant biological activity (FIG. 4).

Discussion

Studies on the structure-activity relationships of the allatostatins indicate that the C-terminal pentapeptide Tyr/Phe-Xaa-Phe-Gly-Leu/Ile-NH$_2$ represents the core sequence required for functional allatostatin activity in vitro (Duve et al., Proc. Natl. Acad. Sci. USA, 90:2456–2460, 1993; Hayes et al. ibid; Pratt et al., 1989, ibid; Pratt et al., 1991, ibid). In terms of the inhibition of JH biosynthesis, the amino acid side chain of Leu was the most important side chain, followed by Phe and Tyr, all of which are located in the C-terminal core sequence. Recent studies have elucidated the primary catabolic cleavage sites of allatostatins following incubation with either soluble enzymes in the hemolymph or with membrane peptidases in crude membrane preparations (Garside et al., Peptides, 18:17–25, 1997; and Garside et al., Gen. Comp. Endocrinol., 108:258–270, 1997). Hemolymph enzymes cleave Dip-AST5 primarily near the N-terminus at Arg-Leu, to yield the C-terminal hexapeptide. This hexapeptide is subsequently cleaved at Leu-Tyr to yield the C-terminal pentapeptide (Garside et al., Peptides, 18:17–25, 1997). Interestingly, these cleavages do not inactivate Dip-AST5 because they do not target sites within the core sequence of the allatostatins. However, the potency of these two catabolites is significantly reduced (Stay et al., Allatostatins, neuropeptide inhibitors of juvenile hormone biosynthesis in brain and corpora allata of the cockroach Diploptera punctata, In: Menn et al., Eds., Insect Neuropeptides, Washington DC, American Chemical Society, 164–176, 1991). For example, the activity of the C-terminal pentapeptide is reduced about 1000-fold (Bendena et al., ibid). Catabolic enzymes in crude membrane preparations of brain, gut and corpora allata cleave allatostatins primarily in the core C-terminal region at Gly-Leu-NH$_2$, with a secondary cleavage site between Tyr-Xaa. Cleavage at the primary site completely inactivates the allatostatin in terms of the inhibition of JH biosynthesis.

Analogs 396-1 and 397-2 were constructed with modifications in the C-terminal 'active core' region of the allatostatins to block degradative cleavage by membrane-bound enzymes. Surprisingly, these analogs showed little resistance to cleavage by membrane-bound enzymes. Nevertheless, the two analogs did block the membrane-bound degradation that would occur at the primary cleavage site within the C-terminal active core pentapeptide region, between Gly-Leu-NH$_2$ in native peptide. The observed cleavage pattern of 396-1 by membrane-bound (brain and midgut) peptidases is consistent with aminopeptidase removal of Ala followed by two consecutive dipeptidyl aminopeptidase-like (DAP) cleavages. In analog 397-2, the two observed cleavages are also consistent with DAP-like removal of successive N-terminal dipeptides. Alternatively, the second cleavage observed with 397-2 (Tyr-Asn) may be catalyzed by a chymotrypsin-like enzyme, because it occurs on the carboxyl side of an aromatic residue.

This N-terminal cleavage pattern observed with analogs 396-1 and 397-2 provided the impetus for the design of analog AST(b)φ2, incorporating the cyclopropyl ring system from 397-2 and a hydrocinnamic acid group, a mimic of the Tyr residue, to 'cap' the N-terminus. This analog effectively removed cleavage sites suggested from incubation of Dip-ASTS with hemolymph enzymes, and those sites targeted by membrane-bound enzymes in native allatostatins and in analog 397-2. The observed results indicate that AST(b)φ2 is the first mimetic analog of an insect neuropeptide with resistance to both hemolymph and tissue-bound peptidases. This analog demonstrated 8-fold and 600-fold longer half-lives than the native neuropeptide Dip-AST5 following exposure to hemolymph and brain peptidases, respectively, and proved to be completely resistant to midgut peptidases.

It is understood that the foregoing detailed description is given merely by way of illustration and that modifications and variations may be made therein without departing from the spirit and scope of the invention.

TABLE 1

Half-life of Dip-AST5 and AST-analogs

| AST/AST-analog | Haemolymph[1] (min) | Brain[2] (min) | Midgut[2] (min) |
|---|---|---|---|
| Dip-AST5 | 153.0 | 18.3 | 67.9 |
| 396-1 | ND | 17.2 | 22.6 |
| 397-2 | ND | 60.9 | 20.8 |
| AsT(b)φ2 | 1214.7 | 10771.5 | ∞ |

Samples were extracted and separated by Phenyl RP-HPLC. Quantity of Dip-AST5 or analog remaining at the end of each incubation was determined by comparison of relative peak area to peak area of authentic Dip-Ast5 at time 0. Half-life was determined following a 1–2 hour incubation period. Values represent the mean of at least 5 assays. ND = not determined. ∞ = no degradation was observed.
[1]Haemolymph was diluted 100 X with saline.
[2]Crude tissue homogenates were prepared at 25 ng protein/μl saline.

TABLE 2 in vitro inhibition of JH biosynthesis by Dip-AST5 and AST analogs

| AST/AST-analog | IC$_{50}$[1] |
|---|---|
| Dip-AST5 | 3.12 × 10$^{-9}$ M |
| 396-1 | 2.12 × 10$^{-9}$ M |
| 397-2 | 1.72 × 10$^{-7}$ M |
| AST(b)φ2 | 1.55 × 10$^{-6}$ M |

[1]IC$_{50}$: Molar concentration of Dip-AST or Dip-AST-analog required for half-maximal inhibition of JH release in a 3 h in vitro radiochemical assay with single 7-day mated CA compared to groups of controls (n > 5).

We claim:

1. A compound of the formula:

R'-X$_1$-X$_a$-X$_b$-X$_2$-NH$_2$ wherein:

(a) R' is selected from the group consisting of Phe, Tyr, a hydrocinnamyl group, a p-hydroxyhydrocinnamic acyl group, and a polypeptide group, which said polypeptide group comprises all or a portion of an allatostatin neuropeptide which is naturally contiguous to the C terminal tetrapeptide X,-Phe-Gly-X$_2$-NH$_2$;

(b) X$_1$ is selected from the group consisting of Asn, Asp, Gly, Ser, and Ala;

(c) X$_2$ is selected from the group consisting of Leu and Ile;

(d) X$_a$, X$_b$ is selected from the group consisting of:
  (i) -Phe-Caa- wherein Caa is a cycloalkyl alanine group selected from the group consisting of cylcopropyl alanine having the structure:

or cyclobutyl alanine having the structure:

(ii) -Aic-Gly- wherein Aic is a 2-amino-indane-2-carboxyl group having the structure:

(iii) -Bzd- wherein Bzd is a 1,4-benzodiazepine group having the structure:

and
  (iv) -Aic-Caa-.

2. The compound of claim 1 wherein R' is Phe or Tyr.

3. The compound of claim 1 wherein R' is a hydrocinnamyl group or a hydroxycinnamyl group.

4. The compound of claim 1 wherein R' is selected from the group consisting of:

Leu-X$_3$-,

Ala-Tyr-Ser-Tyr-Val-Ser-Glu-Tyr-Lys-Arg-Leu-Pro-Val-X$_3$-(SEQ ID No. 8),

Ser-Lys-Met-X$_3$-,

Asp-Gly-Arg-Met-X$_3$-(SEQ ID No. 9),

Asp-Arg-Leu-X$_3$-,

Ala-Arg-Pro-X$_3$-,

Ala-Pro-Ser-Gly-Ala-Gln-Arg-Leu-$X_3$-(SEQ ID No. 10),
Gly-Gly-Ser-Leu-$X_3$-(SEQ ID NO. 11),
Gly-Asp-Gly-Arg-Leu-$X_3$-(SEQ ID No. 12),
Pro-Val-Asn-Ser-Gly-Arg-Ser-Ser-Gly-Ser-Arg-$X_3$-(SEQ ID NO. 13),
Tyr-Pro-Gln-Glu-His-Arg-$X_3$-(SEQ ID NO. 14), and Pro-$X_3$
wherein $X_3$ is Tyr or Phe.

5. The compound of claim 1 wherein $X_a$-$X_b$ is said Phe-cycloalkyl alanine.

6. The compound of claim 3 wherein $X_a$-$X_b$ is said Phe-cycloalkyl alanine.

7. The compound of claim 1 wherein $X_a$-$X_b$ is said Aic-Gly.

8. The compound of claim 3 wherein $X_a$-$X_b$ is said Aic-Gly.

9. The compound of claim 1 wherein $X_a$-$X_b$ is said Aic-Caa.

10. The compound of claim 3 wherein $X_a$-$X_b$ is said Aic-Caa.

11. The compound of claim 1 wherein $X_a$-$X_b$ is said Bzd.

12. The compound of claim 3 wherein $X_a$-$X_b$ is said Bzd.

13. A composition comprising the compound of claim 1 and an inert carrier.

14. The composition of claim 13 wherein said carrier is water.

15. A method for controlling insects comprising applying the compound of claim 1 to the locus of said insects.

16. The method of claim 15 wherein said insects are cockroaches.

17. The method of claim 15 wherein said compound is applied in an amount effective to inhibit or stimulate juvenile hormone production by said insect.

* * * * *

SEQUENCE LISTING

<160> NUMBER OF SEQ ID NOS: 14

<210> SEQ ID NO 1
<211> LENGTH: 13
<212> TYPE: PRT
<213> ORGANISM: Diploptera punctata

<400> SEQUENCE: 1

Ala Tyr Ser Tyr Val Ser Glu Tyr Lys Arg Leu Pro Val
 1               5                  10

<210> SEQ ID NO 2
<211> LENGTH: 4
<212> TYPE: PRT
<213> ORGANISM: Diploptera punctata

<400> SEQUENCE: 2

Asp Gly Arg Met
 1

<210> SEQ ID NO 3
<211> LENGTH: 8
<212> TYPE: PRT
<213> ORGANISM: Diploptera punctata

<400> SEQUENCE: 3

Ala Pro Ser Gly Ala Gln Arg Leu
 1               5

<210> SEQ ID NO 4
<211> LENGTH: 4
<212> TYPE: PRT
<213> ORGANISM: Diploptera punctata

<400> SEQUENCE: 4

Gly Gly Ser Leu
 1

<210> SEQ ID NO 5
<211> LENGTH: 5
<212> TYPE: PRT
<213> ORGANISM: Diploptera punctata

<400> SEQUENCE: 5

Gly Asp Gly Arg Leu
 1               5

<210> SEQ ID NO 6
<211> LENGTH: 11
<212> TYPE: PRT
<213> ORGANISM: Diploptera punctata

<400> SEQUENCE: 6

Pro Val Asn Ser Gly Arg Ser Ser Gly Ser Arg
 1               5                  10

<210> SEQ ID NO 7
<211> LENGTH: 6
<212> TYPE: PRT
<213> ORGANISM: Diploptera punctata

<400> SEQUENCE: 7

Tyr Pro Gln Glu His Arg

<210> SEQ ID NO 8
<211> LENGTH: 14
<212> TYPE: PRT
<213> ORGANISM: Diploptera punctata
<220> FEATURE:
<221> NAME/KEY: VARIANT
<222> LOCATION: (14)
<223> OTHER INFORMATION: May be Tyr or Phe

<400> SEQUENCE: 8

Ala Tyr Ser Tyr Val Ser Glu Tyr Lys Arg Leu Pro Val Xaa
 1               5                  10

<210> SEQ ID NO 9
<211> LENGTH: 5
<212> TYPE: PRT
<213> ORGANISM: Diploptera punctata
<220> FEATURE:
<221> NAME/KEY: VARIANT
<222> LOCATION: (5)
<223> OTHER INFORMATION: May be Tyr or Phe

<400> SEQUENCE: 9

Asp Gly Arg Met Xaa
 1               5

<210> SEQ ID NO 10
<211> LENGTH: 9
<212> TYPE: PRT
<213> ORGANISM: Diploptera punctata
<220> FEATURE:
<221> NAME/KEY: VARIANT
<222> LOCATION: (9)
<223> OTHER INFORMATION: May be Tyr or Phe

<400> SEQUENCE: 10

Ala Pro Ser Gly Ala Gln Arg Leu Xaa
 1               5

<210> SEQ ID NO 11
<211> LENGTH: 5
<212> TYPE: PRT
<213> ORGANISM: Diploptera punctata
<220> FEATURE:
<221> NAME/KEY: VARIANT
<222> LOCATION: (5)
<223> OTHER INFORMATION: May be Tyr or Phe

<400> SEQUENCE: 11

Gly Gly Ser Leu Xaa
 1               5

<210> SEQ ID NO 12
<211> LENGTH: 6
<212> TYPE: PRT
<213> ORGANISM: Diploptera punctata
<220> FEATURE:
<221> NAME/KEY: VARIANT
<222> LOCATION: (6)
<223> OTHER INFORMATION: May be Tyr or Phe

<400> SEQUENCE: 12

Gly Asp Gly Arg Leu Xaa
 1               5

<210> SEQ ID NO 13

```
<211> LENGTH: 12
<212> TYPE: PRT
<213> ORGANISM: Diploptera punctata
<220> FEATURE:
<221> NAME/KEY: VARIANT
<222> LOCATION: (12)
<223> OTHER INFORMATION: May be Tyr or Phe

<400> SEQUENCE: 13

Pro Val Asn Ser Gly Arg Ser Ser Gly Ser Arg Xaa
 1               5                  10

<210> SEQ ID NO 14
<211> LENGTH: 7
<212> TYPE: PRT
<213> ORGANISM: Diploptera punctata
<220> FEATURE:
<221> NAME/KEY: VARIANT
<222> LOCATION: (7)
<223> OTHER INFORMATION: May be Tyr or Phe

<400> SEQUENCE: 14

Tyr Pro Gln Glu His Arg Xaa
 1               5
```